(12) United States Patent
Madsen

(10) Patent No.: US 11,577,016 B2
(45) Date of Patent: Feb. 14, 2023

(54) SYSTEM AND METHOD FOR IRRADIATING BIOLOGICAL FLUIDS

(71) Applicant: Fenwal, Inc., Lake Zurich, IL (US)

(72) Inventor: James Madsen, Chicago, IL (US)

(73) Assignee: Fenwal, Inc., Lake Zurich, IL (US)

(*) Notice: Subject to any disclaimer, the term of this patent is extended or adjusted under 35 U.S.C. 154(b) by 280 days.

(21) Appl. No.: 16/945,378

(22) Filed: Jul. 31, 2020

(65) Prior Publication Data

US 2021/0052804 A1 Feb. 25, 2021

Related U.S. Application Data

(60) Provisional application No. 62/889,233, filed on Aug. 20, 2019.

(51) Int. Cl.
| | | |
|---|---|---|
| *A61M 1/36* | (2006.01) | |
| *A61L 2/00* | (2006.01) | |
| *A61L 2/10* | (2006.01) | |

(52) U.S. Cl.
CPC ......... *A61M 1/3681* (2013.01); *A61L 2/0047* (2013.01); *A61M 1/3693* (2013.01); *A61L 2/10* (2013.01); *A61L 2202/11* (2013.01); *A61L 2202/22* (2013.01)

(58) Field of Classification Search
CPC . A61M 1/3681; A61M 1/3693; A61L 2/0047; A61L 2/10; A61L 2202/11; A61L 2202/22
USPC .................................................... 250/455.11
See application file for complete search history.

(56) References Cited

U.S. PATENT DOCUMENTS

| | | | |
|---|---|---|---|
| 5,360,542 | A | 11/1994 | Willianson, IV et al. |
| 5,527,704 | A | 6/1996 | Wolf, Jr. et al. |
| 5,762,867 | A | 6/1998 | D'Silva |
| 5,868,696 | A | 2/1999 | Giesler et al. |
| 6,369,394 | B1 | 4/2002 | Lee |
| 7,433,030 | B2 | 10/2008 | Waldo et al. |
| 8,339,592 | B2 | 12/2012 | Hlavinka et al. |
| 2003/0205454 | A1 | 11/2003 | Hlavinka et al. |

(Continued)

FOREIGN PATENT DOCUMENTS

EP 3053616 8/2016

OTHER PUBLICATIONS

Extended European Search Report, counterpart European App. No. 20190975.1 (dated Jan. 29, 2021) (7 pages).

(Continued)

*Primary Examiner* — Kiet T Nguyen
(74) *Attorney, Agent, or Firm* — Cook Alex Ltd.

(57) ABSTRACT

An irradiation device includes a fluid treatment chamber having first and second opposing sides configured to receive a biological fluid container therebetween, and at least one light source disposed adjacent at least one of the first and second sides of the fluid treatment chamber. The at least one light source includes a light guide having a front planar surface that defines in part the at least one of the first and second sides of the fluid treatment chamber, and at least one light emitting diode (LED) disposed at an edge of the light guide outside the fluid treatment chamber and configured to direct light into the light guide. The light guide has a back surface opposite the front planar surface, the back surface with one or more reflectors that depend into the light guide in the direction of the front surface.

20 Claims, 7 Drawing Sheets

(56) References Cited

U.S. PATENT DOCUMENTS

2019/0170734 A1* 6/2019 Chou ............... G01N 21/6486
2020/0378886 A1* 12/2020 Chou ................... G01N 33/49

OTHER PUBLICATIONS

Kim et al., Optimized pattern design of light-guide plate (LGP), Optica Applicata, vol. XLI, No. 4, 863-72 (2011).

* cited by examiner

SYSTEM AND METHOD FOR IRRADIATING BIOLOGICAL FLUIDS

TECHNICAL HELD

This application claims the benefit of U.S. Provisional Patent App. No. 62/889,233, filed Aug. 20, 2019, which is expressly incorporated herein by reference in its entirety.

TECHNICAL FIELD

The present disclosure is generally directed to a system and method for processing a biological fluid, and in particular a biological fluid processing system or method where the processing includes irradiation of the biological fluid.

BACKGROUND

Biological fluid processing systems may be configured to process biological fluid, such as may be drawn from a patient, to provide a product that may be returned to the patient, for example. These processing systems may include a reusable processor or separator, as well as a disposable fluid circuit or set. According to certain systems, the circuit or set may be connected to the patient to exchange fluids with the patient. The set may also be connected to various containers that include other fluids, such as wash solutions and the like.

During the processing, the biological fluid may be combined with a photoactive compound, and then the fluid may be exposed to ultraviolet (UV) light. For example, the fluid may contain mononuclear cells (MNC), and may be combined with 8-methoxypsoralen ("8-MOP"). It is believed that the combination of 8-MOP and the photoactivation causes apoptosis, or programmed cell death, of T-cells.

At present, the MNC is collected in a long flexible container or bag that is disposed in a photoactivation device, such as is illustrated in U.S. Pat. No. 7,433,030. These long flexible containers are irradiated using long UV bulbs, which bulbs are disposed parallel to the container, typically both above and below the container. Further, the length of the UV bulbs and the length of the flexible container is approximately the same, Because of the use of large numbers of long UV bulbs, these photoactivation devices may make high power demands, resulting in added expense.

The photoactivation devices typically also include some form of mixing mechanism to mix the fluid in the container, because the cells nearer the surface of the container, and thus nearer the UV bulbs, receive a higher dose of radiation than cells in the center of the container. In addition, care is required to ensure an even thickness to reduce the likelihood of formation of hot and cold regions in the container during photoactivation. Because of the issues with conventional technology, and particular those issues relating to maintaining an even fluid thickness, the volume of biological fluid treated using such technology may be limited.

SUMMARY

There are several aspects of the present subject matter that may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In a first aspect, an irradiation device includes a fluid treatment chamber having first and second opposing sides configured to receive a biological fluid container therebetween, and at least one light source disposed adjacent at least one of the first and second sides of the fluid treatment chamber. The at least one light source includes a light guide having a front planar surface that defines in part the at least one of the first and second sides of the fluid treatment chamber, and at least one light emitting diode (LED) disposed at an edge of the light guide outside the fluid treatment chamber and configured to direct light into the light guide. The light guide has a back surface opposite the front planar surface, the back surface with one or more reflectors that depend into the light guide in the direction of the front surface.

In a second aspect, a system includes a cell separator configured to direct a biological fluid into a biological fluid container, and an irradiation device. The irradiation device includes a fluid treatment chamber having first and second opposing sides configured to receive the biological fluid container therebetween, and at least one light source disposed adjacent at least one of the first and second sides of the fluid treatment chamber. The at least one light source includes a light guide having a front planar surface that defines in part the at least one of the first and second sides of the fluid treatment chamber, and at least one light emitting diode (LED) disposed at an edge of the light guide outside the fluid treatment chamber and configured to direct light into the light guide. The light guide has a back surface opposite the front planar surface, the back surface with one or more reflectors that depend into the light guide in the direction of the front surface.

DETAILED DESCRIPTION

A detailed description of the systems and methods in accordance with the present disclosure is set forth below. It should be understood that the description below of specific devices and methods is intended to be exemplary, and not exhaustive of all possible variations or applications. Thus, the scope of the disclosure is not intended to be limiting, and should be understood to encompass variations or embodiments that would occur to persons of ordinary skill.

Figure 1:
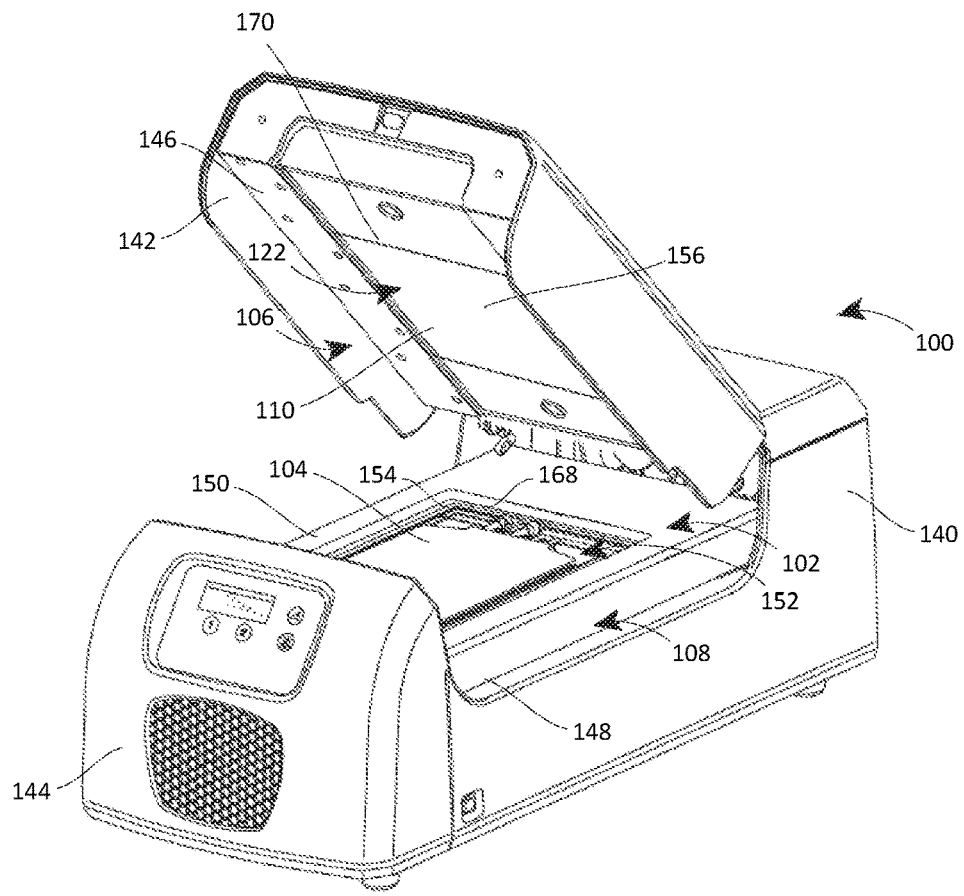
FIG. 1 is a perspective view of an irradiation device according to an embodiment of the present disclosure.
Figure 2:
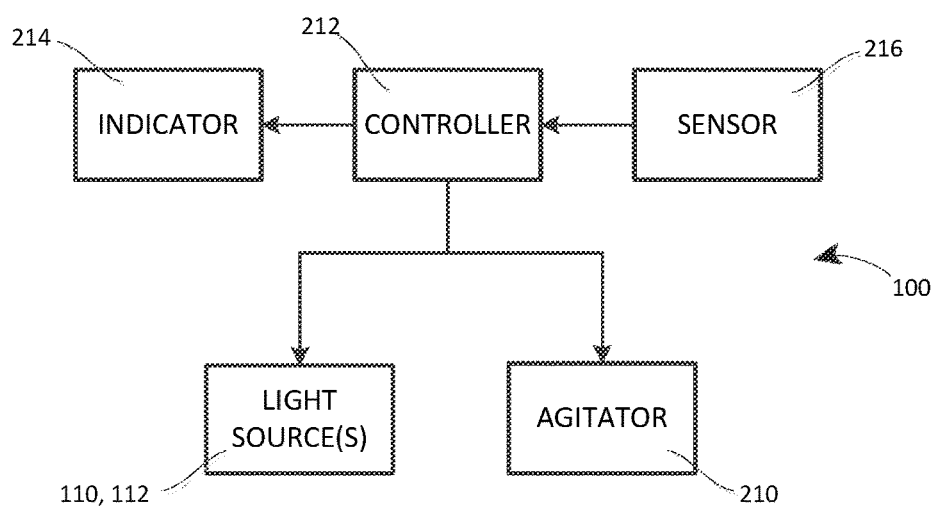
FIG. 2 is a block diagram of the irradiation device according to FIG. 1.
Figure 3:
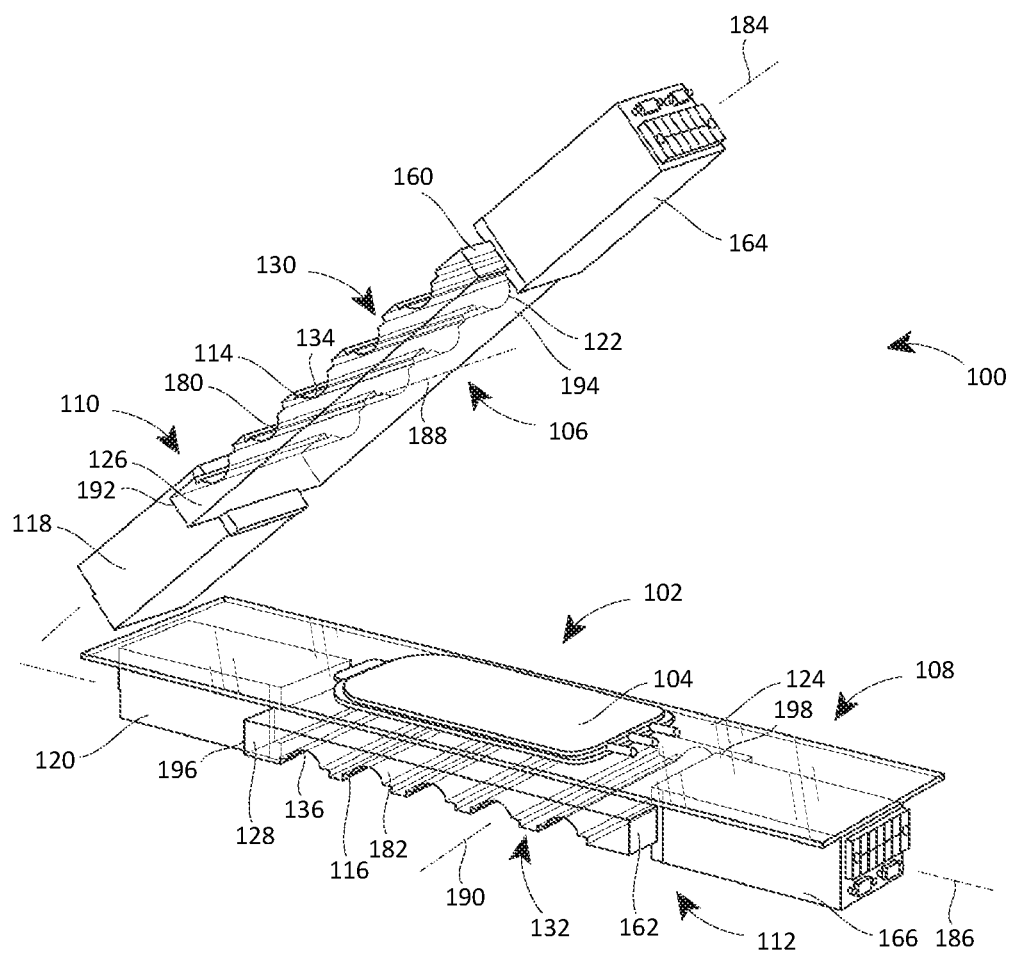
FIG. 3 is a perspective view of the light sources of the irradiation device of FIG. 1, with the housing removed and the light sources in a first position, spaced to permit a biological fluid container to be disposed therebetween or to be removed therefrom.
Figure 4:
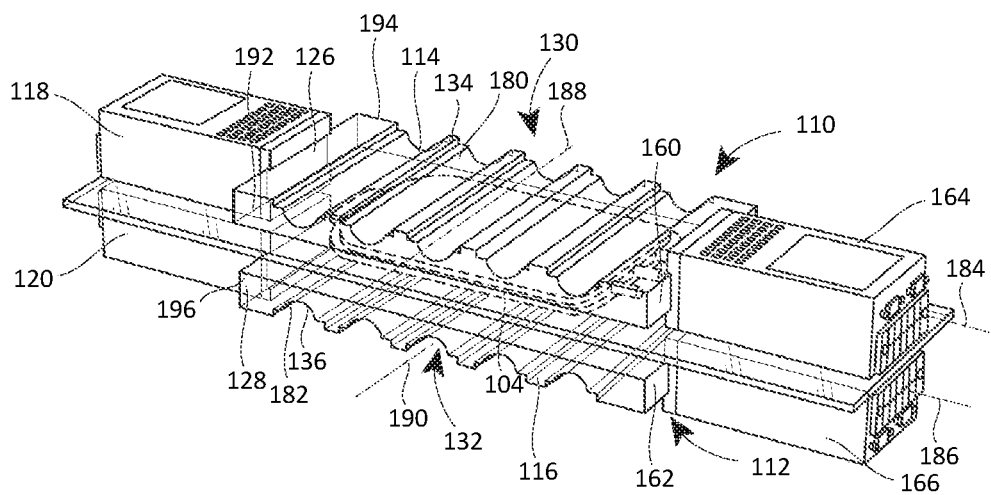
FIG. 4 is a perspective view of the light sources of FIG. 3, with the light sources in a second position, with the biological fluid container disposed therebetween for treatment.

As illustrated in FIGS. 1, 3, and 4, an irradiation device 100 includes a fluid treatment chamber 102 configured to receive a biological fluid container 104, fluid treatment chamber 102 having opposing first and second sides 106, 108. As illustrated in FIGS. 2-4, the device 100 also includes at least one light source 110 disposed adjacent at least one of first and second sides 106, 108 of the fluid treatment chamber 102. As illustrated, in FIGS. 3 and 4, the device 100 includes a first light source 110 adjacent the first side 106, and a second light source 112 adjacent the second side 108.

Figure 5:
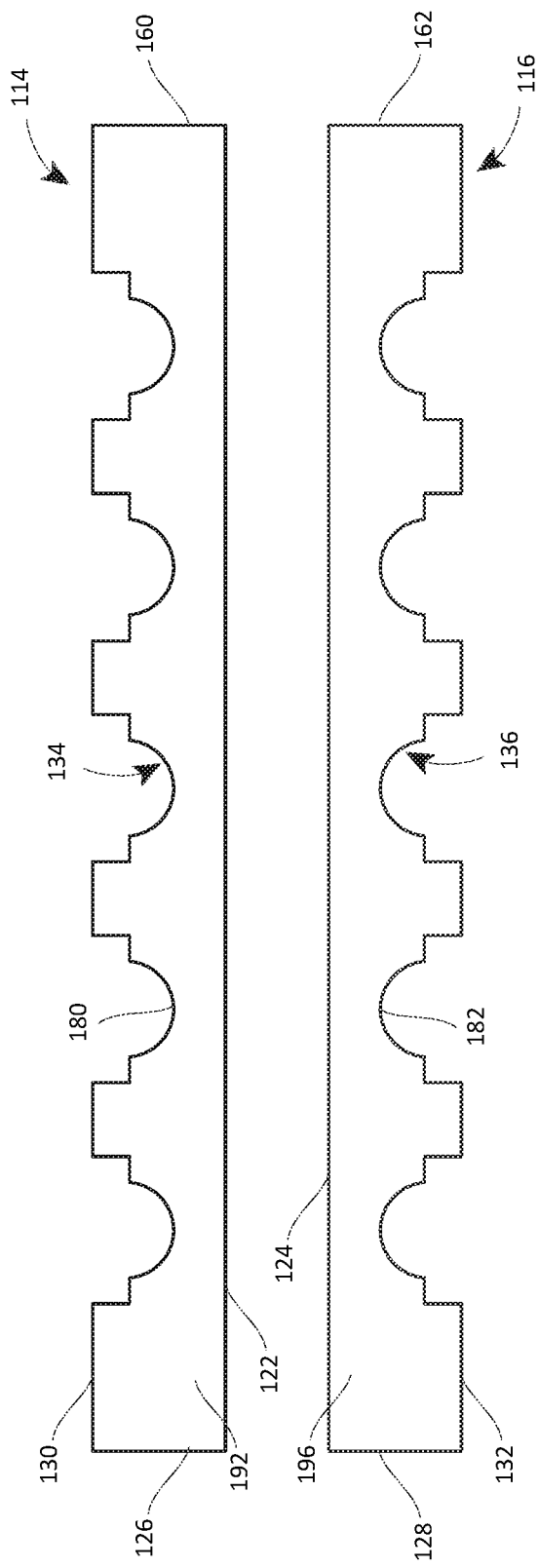
FIG. 5 is an enlarged, side view of the light guides used in the light sources of FIGS. 3 and 4.

The light source 110, 112 of FIGS. 3 and 4 includes a light guide 114, 116 and at least one light emitting diode (LED) 118, 120. The light guide having 114, 116 has a front planar surface 122, 124 that defines in part the at least one of the first and second sides 106, 108 of the fluid treatment chamber 102. The at least one LED 118, 120 is disposed at an edge 126, 128 of the light guide 114, 116 outside the fluid treatment chamber 102 and configured to direct light into the light guide 114, 116. The light guide 114, 116 has a back surface 130, 132 opposite the front planar surface 122, 124, the back surface 130, 132 with one or more reflectors 134, 136 that depend into the light guide 114, 116 in the direction of the front surface 122, 124. See also FIG. 5. The reflectors 134, 136 bend and distribute light from the LEDs 118, 120 such that at least some portion of the light traveling along the light guide 114, 116 is directed out of the light guide 114, 116 through the surface 122, 124.

As illustrated in FIG. 1, the device 100 may also include a housing 140 in which the fluid treatment chamber 102 is defined, and in which the light sources 110, 112 are disposed. The embodiment of housing 140 in FIG. 1 includes a lid 142 that may be pivotally attached to a base 144 and moved to open housing 140 and permit access to fluid treatment chamber 102. The lid 142 has a lid surface 146 and base 144 has a base surface 148, the lid surface 146 defining, at least in part, the first opposing side 106 of the fluid treatment chamber 102, and the base surface 148 defining, at least in part, the second opposing side 108 of the fluid treatment chamber 102. While FIG. 1 illustrates an embodiment of housing 140 including a lid 142 and a base 144, it will be recognized that according to other embodiments of device 100, housing 140 may instead include a sliding drawer that permits access to fluid treatment chamber 102.

The device 100 may be operated as follows. The lid 142 may be opened relative to the base 144 by pivoting the lid 142 upward, a biological fluid container 104 may be disposed on the surface 124 between the lid 142 and the base 144, and the lid 142 may be closed relative to the base 144. The light source 110, 112 may be activated, thereby irradiating biological fluid container 104 in fluid treatment chamber 102. The light source 110, 112 may be deactivated once the treatment is complete, or sooner if an error occurs (e.g., the container 104 leaks or the temperature in the chamber 102 exceeds a threshold). The lid 142 may then be opened relative to the base 144, and the container 104 may be removed.

The device 100 may have one or more advantages relative to existing devices for treating a container of cells with light, in particular with (but not limited to) UV light. It is believed that the size of a light source including at least one LED and a light guide can be reduced significantly relative to existing UV light bulbs, while providing similar performance, permitting the device footprint to be reduced. In addition, the light guide does not produce heat as the existing UV light bulbs do, and thus the container can be brought into closer proximity or contact with the light source 110, 112 (particularly where the LEDs associated with the light guide are disposed outside the treatment chamber). This also is believed to permit the space requirements of the device 100 to be reduced, further limiting the device footprint. Additionally, it is believed that the LEDs used in a light source 110, 112 will have lower power requirements than the existing UV light bulbs, reducing the cost of treatment presently and in the future as improvements are made in LED technology. Further, it is believed that LEDs will have a longer life than existing UV light bulbs, providing for a cost savings relative existing technology over time. Moreover, LEDs may be selected or designed to provide a narrow bandwidth of radiation, and it is believed that the more tailored emission spectrum possible could lead to more efficient photoactivation. In a similar fashion, the configuration of the reflectors within the light guide may be selected or designed to provide controlled application of radiation (light), which may have the further effect of limiting or eliminating variations in the radiation applied. This could lead to the reduction or elimination of the need for agitation of the container.

Having described the general structure and operation of the irradiation device 100, the details of the structure and operation now may be discussed.

As illustrated, in FIG. 1, the fluid treatment chamber 102 may be defined, at least in part, by a tray 150, the light sources 110, 112 (and in particular, the light guides 114, 116) and the housing 140 also assisting in defining the fluid treatment chamber 102, as explained below. The tray 150 may be made of a polymeric material in part, with certain sections of the tray 150 made of another material, such as glass. In an alternate embodiment, the tray 150 may be omitted or optional.

The tray 150 may have a recess or pocket 152 that may be used to retain any fluid leaking from the container 104, and the recess 152 may have a translucent floor 154 configured to be disposed between the at least one light source 110, 112 and the biological fluid container 104. The floor 154 may be translucent to permit the illumination of the biological fluid container 104 on both sides, where, as in the illustrated embodiment, the light sources 110, 112 are disposed on either side of the tray 150, and thus on either side 106, 108 of the fluid treatment chamber 102. The floor 154 may be made of glass. In an embodiment of the irradiation device 100 where the container 104 is illuminated on only one side, the floor 154 may be non-translucent.

The light sources 110, 112 may be disposed in the lid 142 and the base 144, respectively, with the light source 110 disposed adjacent the first side 106 of the fluid treatment chamber 102, and the light source 112 disposed adjacent the second side 108 of the fluid treatment chamber 102. In particular, the light source 110 may be disposed in the lid 142 such that the light guide 114 is aligned with or define a translucent window 156 in the lid 142, and the light source 112 may be disposed in the base 144 such that the light guide 116 is aligned with the translucent floor 154 of the tray 150, which itself may be aligned with a translucent window in the base 144, or the light guide 116 itself. The edge 126, 128 may be disposed to one side of the floor 154 or the window 156 such that the LED 118, 120 is disposed outside the fluid treatment chamber. This can be seen better relative to FIGS. 3 and 4.

In addition to the front surface 122, 124, the edge 126, 128, and the back surface 130, 132, the light guides 114, 116 also include edges 160, 162 opposite the edges 126, 128. LEDs 164, 166 are disposed at the edges 160, 162 with the LEDs 118, 120 facing the LEDs 164, 166 along the light guide 114, 116. With the edges 126, 128, 160, 162 aligned with edges 168, 170 of the floor 154 and the window 156, the LEDs 118, 120, 164, 166 may be disposed outside the fluid treatment chamber.

As thus disposed, the reflectors 134, 136 of the light guides 114, 116 are aligned with the floor 154 and the window 156. According to the illustrated embodiment, the reflectors 134, 136 may be defined by at least one hemicylindrical shape 180, 182 that depends into the light guide 114, 116 from the back surface 130, 132 in the direction of the front surface 122, 124. As illustrated, the reflectors 134, 136 may include a plurality (e.g., five as illustrated) of the hemicylindrical shapes 180, 182. According to other embodiments, different shapes or different numbers of the reflectors 134, 136 may be used to bend and distribute light from the LEDs 118, 120 such that at least some portion of the light traveling along the light guide 114, 16 is directed out of the light guide 114, 116 through the surface 122, 124 in a manner controlled through the design or selection of the reflectors 134, 136.

The light guides 114, 116 each have a first axis 184, 186 along which the LEDs 118, 184, 120, 166 are disposed. Given the shape of the light guides 114, 116 illustrated in FIGS. 3 and 4, the first axis 184, 186 may also be referred to as a longitudinal axis. The light guides 114, 116 also each have a second axis 188, 190 that is transverse to the first axis 184, 188. As illustrated, the second axes 188, 190 are orthogonal to the first axes 184, 188, and given the shape of the light guides 114, 116, each second axis 188, 190 may be referred to as a lateral axis. The hemicylindrical shapes 180, 182 are disposed along or parallel to the second axis 188, 190.

Each light guide 114, 116 may have opposing first and second ends 192, 194, 196, 198. See, e.g., FIG. 3. The first and second ends 192, 194, 196, 198 may be disposed facing each other along the second axis 188, 190. Further, the hemicylindrical shape 180, 182 may be disposed along the second axes 188, 190 continuously between the first and second ends 192, 194, 196, 198. According to other embodiments, the shapes may instead be discontinuous along the axis 188, 190 between the first and second ends 192, 194, 196, 198 (i.e., the shape may have one or more discontinuities therein).

Further, the hemicylindrical shapes 180, 182 may be disposed along the back surface 130, 132 with equal spacing between the shapes 180, 182 in the direction of the first (longitudinal) axis 184, 186. This may also be referred to as the shapes 180, 182 being equally disposed along the back surface 130, 132. According to other embodiments, one or more of the shapes 180, 182 may be closer to at least one of the adjacent shapes 180, 182 than others of the shapes 180, 182. In fact, the spacing of the shapes 180 182 may vary along the axes 184, 186 between the edges 126, 128, 160, 162.

The LEDs 118, 120, 164, 166 may be a UV light-emitting LED according to the illustrated embodiment. According to other embodiments, the LEDs may emit other wavelengths of light. Further, the LEDs 118, 120, 164, 166 may include a single LED, or an array of LEDs.

As is illustrated in FIG. 2, the device 100 may include additional equipment as well.

An agitator 210 may be coupled to fluid treatment chamber 102 to move the container 104 and/or at least a part of fluid treatment chamber 102 with an oscillatory motion. As mentioned above, the light guide and/or LED may be selected or designed to reduce localizations within the radiation distribution, but it may still be desirable to include an agitator 210 to improve mixing of the contents of the container 104. Agitator 210 may include a motor in combination with a linkage (such as a rotating cam), the linkage coupling the motor to the tray 150, for example. An embodiment of an agitator is described in the afore-mentioned U.S. Pat. No. 7,433,030, which has been incorporated herein. The agitator 210 may cause the biological fluid container 104 disposed in the tray 150, to move in an oscillatory fashion over a distance of 2.54 cm (1 inch) at a frequency of 1 Hz according to one such embodiment.

A controller 212 may also be disposed in housing 140. While controller 212 may include one or more electrical components or circuits, controller 212 may include in addition or instead a processor and an associated memory according to one embodiment. According to such an embodiment, the processor may be programmed to carry out any of the actions that controller 212 is described as being configured to perform. The instructions by which the processor is programmed may be stored on the memory associated with the processor, which memory may include one or more tangible non-transitory computer readable memories, having computer executable instructions stored thereon, which when executed by the processor, may cause the one or more processors to carry out one or more actions.

For example, the controller 212 may be coupled to the light sources 110, 112 and the agitator 210. The controller 212 may be configured to automatically activate and to automatically deactivate the light source 110, 112. Further, where the device 100 includes an agitator 210, the controller 212 may be configured to automatically activate and to automatically deactivate the agitator 210.

As a further example, once the controller 212 determines that a cycle should begin, the controller 212 activates the light source(s) 110, 112, thereby irradiating the biological fluid container 104 in the fluid treatment chamber 102. According to certain embodiments, the controller 212 also may activate the agitator 210, thereby agitating the biological fluid container 104 while the biological fluid container 104 is irradiated. While irradiation may be initiated before agitation, this need not be the case according to all embodiments: initiation of agitation may precede irradiation, or the two may be initiated as approximately the same time (i.e., "simultaneously").

The device 100 also may include an indicator 214. The controller 212 may be coupled to the indicator 214, one example of which is a light, such as a light emitting diode, disposed on or outside the housing 140 to be visible to the operator. The indicator 214 may be used to provide an indication to the operator that the cycle should be terminated (manually by the operator), that the cycle will be terminated (automatically by controller 212), or that the cycle is complete.

The indicator 214 may take other forms of visible indicator, such as a display screen. The indicator 214 may also take the form of an audible indicator, such as a buzzer of other sound-producing element. The indicator 214 may be a combination of one or more of such visible and audible indicators and may include additional devices as well.

The device 100 may also include one or more sensors 216. The sensor(s) 216 may be coupled to the controller 212, and may provide data to the controller 212. For example, a moisture sensor may be used to determine if the container 104 is leaking into the tray 150. Alternatively, a temperature sensor (e.g., thermocouple) may be used to determine if the temperature in the chamber 102 has exceeded a threshold. Other sensors may be used with the device 100 as well.

Figure 6:
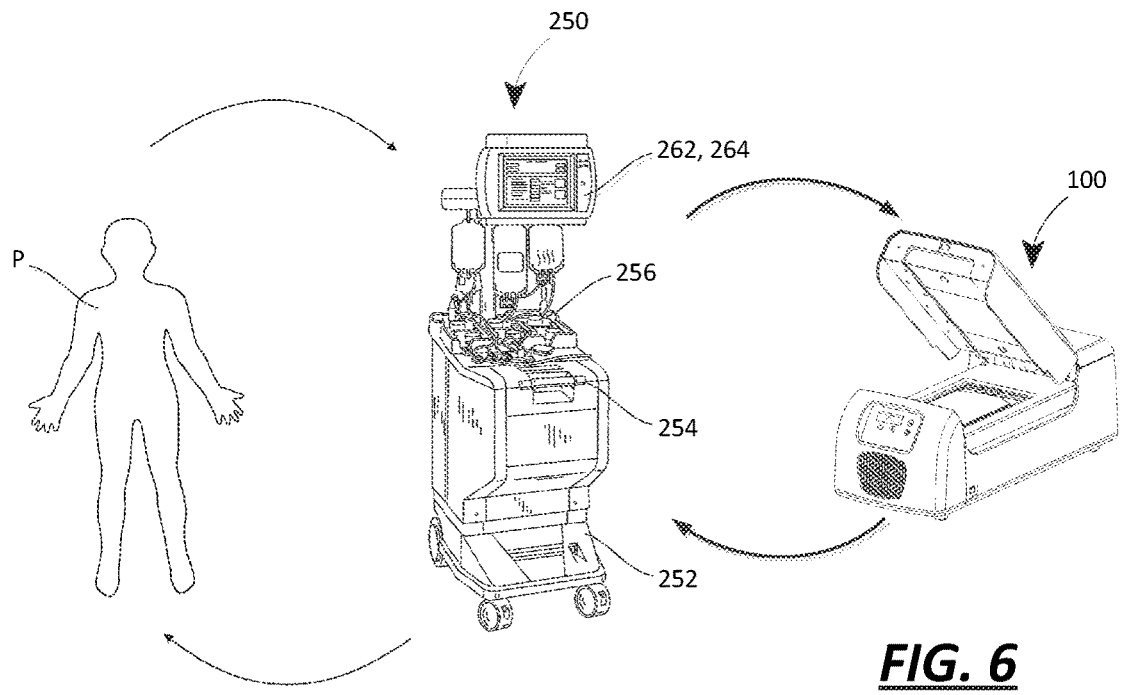
FIG. 6 a schematic diagram of an embodiment of a medical system including a reusable apparatus, a disposable processing set or fluid circuit mounted on or to the reusable apparatus, and an irradiation device.
Figure 7:
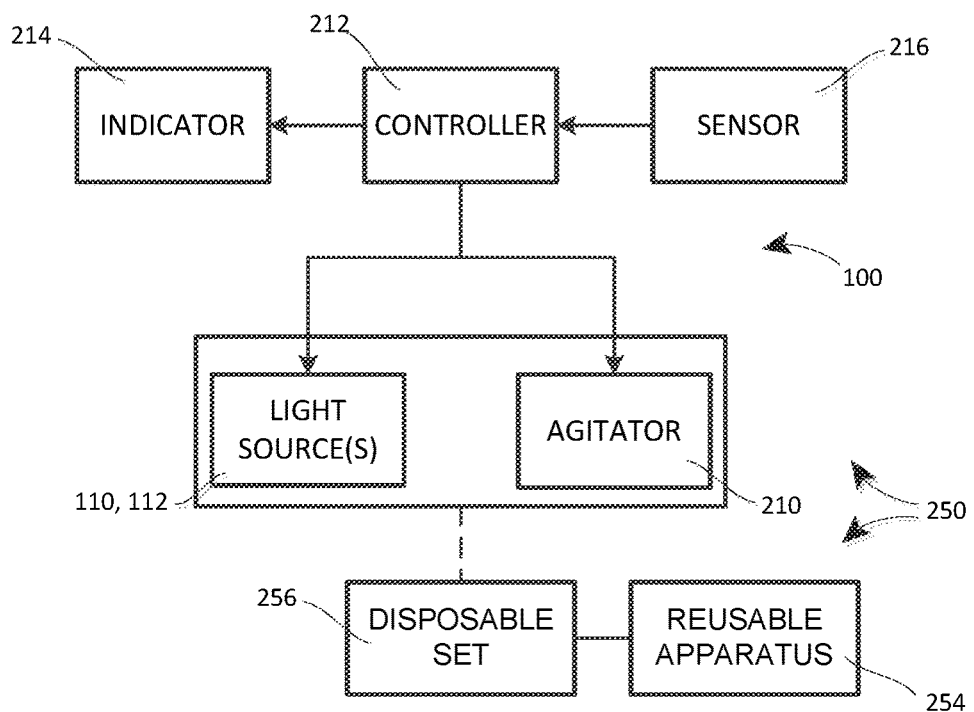
FIG. 7 is a block diagram of the medical system according to FIG. 6.

While the irradiation device 100 may be used independent and apart from equipment that takes a biological fluid and separates it into components, the irradiation device 100 may also be used as part of a system for processing a biological fluid. As illustrated in FIGS. 6 and 7, such a system 250 may include a cell separator 252 configured to separate a biological fluid into at least two streams of cell components, for example using a centrifugal separator, a spinning membrane, etc. Further, the system 250 may include an irradiation device 100. The processing container 104 of the irradiation device 100 may be couplable to the cell separator 252 to receive the cell components of at least one of the at least two streams.

All of the discussion regarding the various embodiments of the irradiation device 100 above may apply to the irradiation device 100 included as part of the system 250, as indicated generally in FIGS. 6 and 7. As also indicated in FIG. 7, the cell separator 252 may include a reusable apparatus 254 and a disposable fluid circuit 256 mounted to or on the reusable apparatus 254, the fluid circuit 256 couplable to the processing container 104. According to certain embodiments, the processing container 104 also is detachable from the fluid circuit 256.

Figure 8:
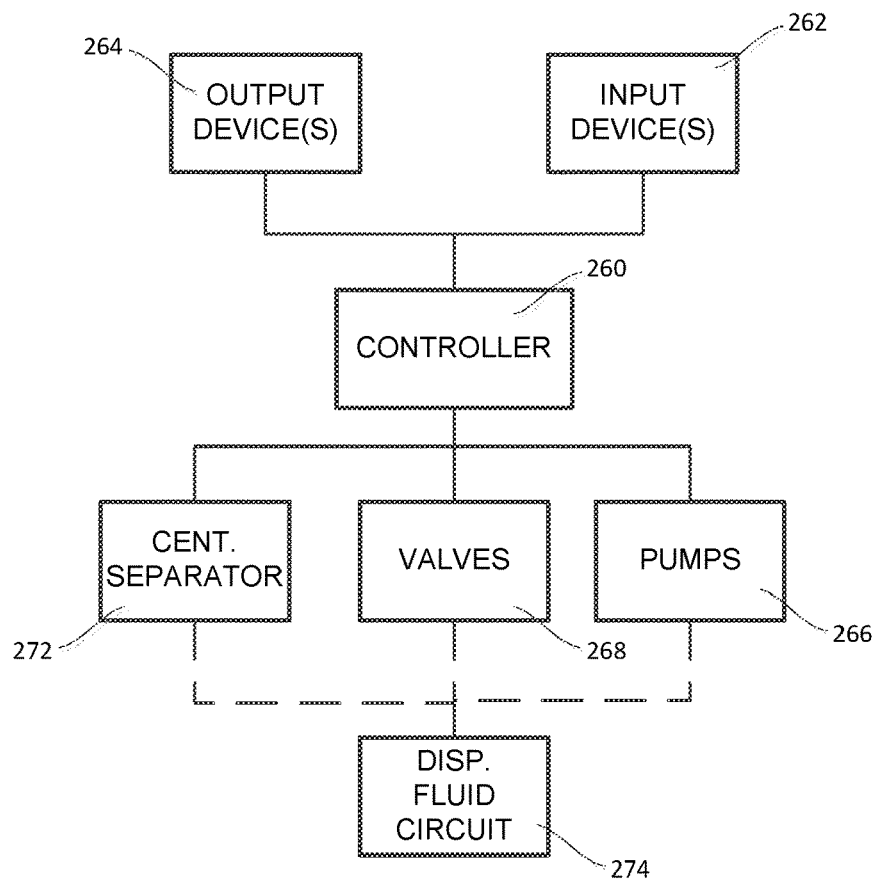
FIG. 8 is a block diagram of an embodiment of a reusable apparatus and a disposable set as may be part of the medical system according to FIG. 6.
Figure 9:
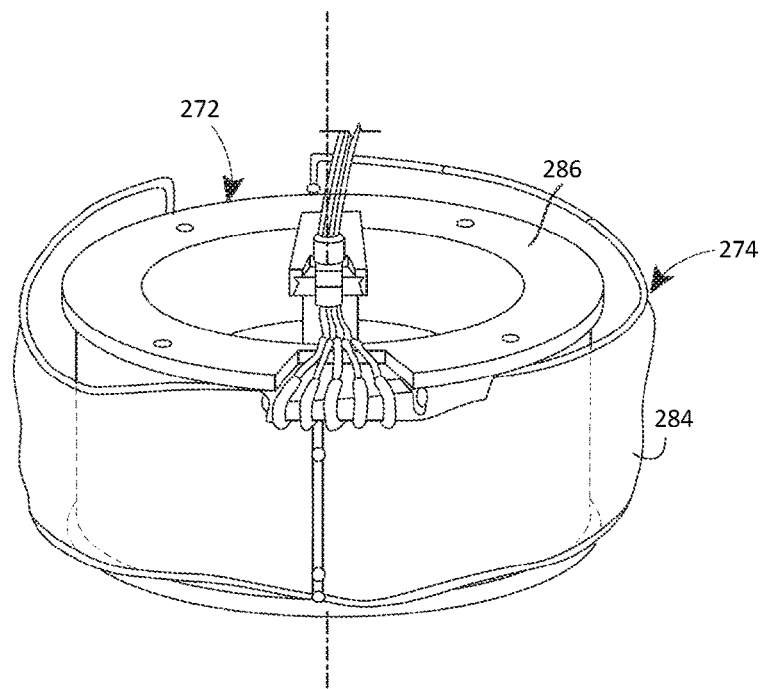
FIG. 9 is a schematic diagram of a sub-system of the reusable apparatus of FIG. 8.
Figure 10:
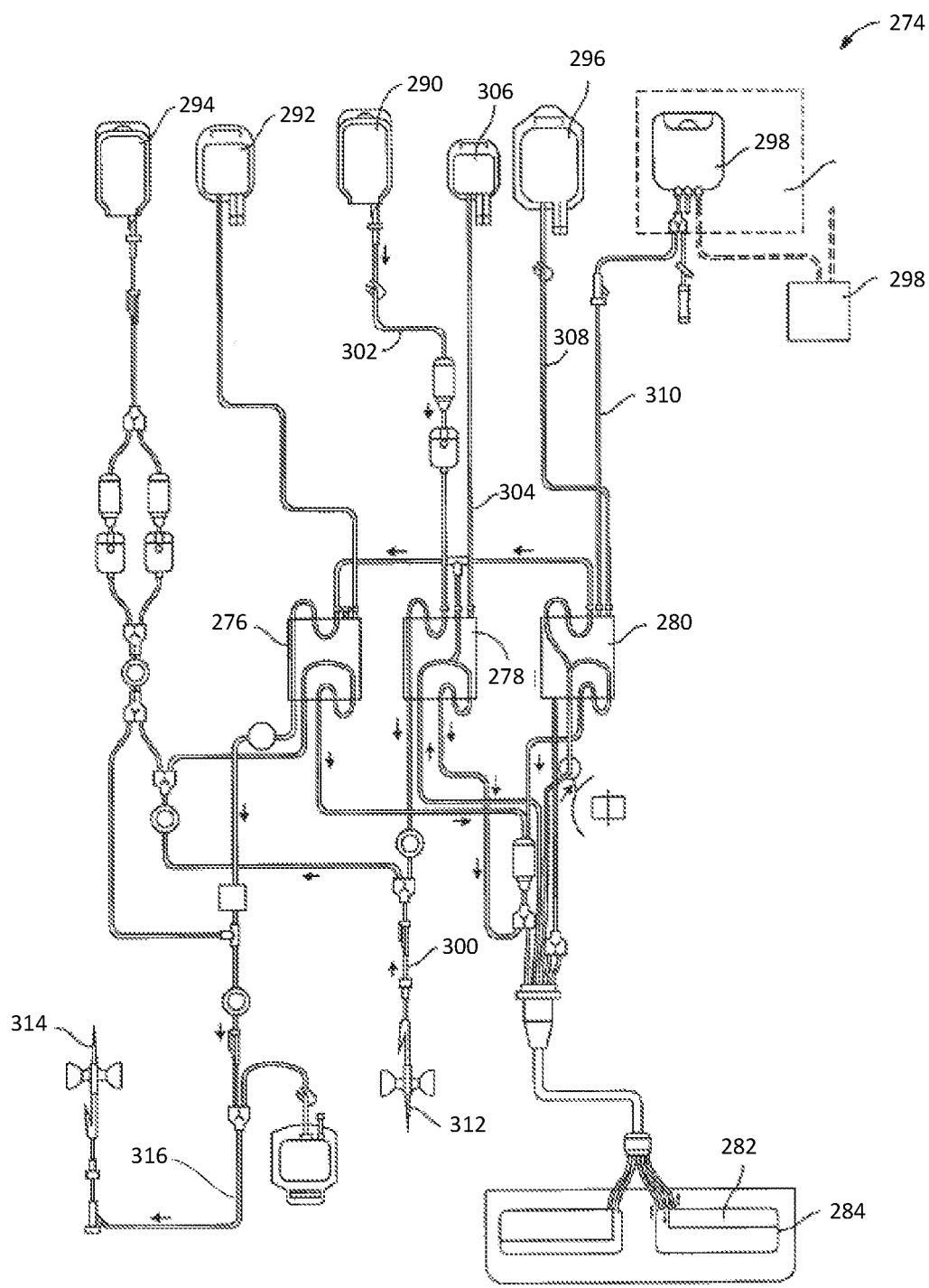
FIG. 10 is a schematic diagram of the disposable set of FIG. 8.

According to one embodiments of the medical system 250, the reusable device 254 may be an AMICUS® Separator, available from Fresenius Kabi USA, Lake Zurich, Ill., configured to carry out apheresis, for example. Briefly, FIGS. 8-10 show such an embodiment of an apparatus 252, with FIG. 8 illustrating the structures of the apparatus 254 schematically, FIG. 9 illustrating a representative blood centrifuge (defining part of the cell separator 252) with a portion of a fluid circuit mounted thereon (which fluid circuit also may define part of the cell separator 252, and may be an embodiment of the fluid circuit 256), and FIG. 10 illustrating the remainder of the fluid circuit. Additional details of the interaction of such an apparatus and a set are discussed in U.S. Pat. No. 5,868,696, which is incorporated by reference herein in its entirety.

With reference first to FIG. 8, the illustrated embodiment of the apparatus 254 thus may include a controller 260, which may be configured as the controller 212 discussed above, and in particular may be configured to carry out one (or more) of the embodiments of the method discussed herein. The apparatus also includes an input device 262 in the form of a touch screen and an output device 264 in the form of an electronic display. The input devices 262 according to this embodiment may further include sensors (or sensor stations), such as weight scales, pressure sensors and air detectors. The controller 260 is coupled to the input devices 262 and the output device 264, as well as to a plurality of pumps 266 (e.g. peristaltic pumps), a plurality of valves (or valve stations) 268, and a centrifugal separator 272. Mounted on the pumps 266, the valves 268, and the separator 272 (which along with the sensors 262 may together define an embodiment of an interface) is a fluid circuit 274, which may be an embodiment of the fluid circuit 256. The controller 260 is configured (e.g., programmed) to control each of the pumps 266, valves 268, and the centrifugal separator 272 to carry out an instance of a procedure in combination with the fluid circuit 274.

Processing set (also referred to as a fluid circuit) 274 includes a plurality of processing fluid flow cassettes 276, 278, 280 (see FIG. 10) with tubing loops for association with peristaltic pumps 266. Set 274 also includes a network of tubing and connected (or pre-connected) containers for establishing flow communication with the patient and for processing and collecting fluids and blood and blood components, as discussed in detail below. The set 274 also includes a separation chamber 282.

As illustrated in FIGS. 9 and 10, the separation chamber 282 is defined by the walls of a flexible processing container 284 carried within an annular gap defined by a rotating spool element 286 (see FIG. 9) and an outer bowl element of the device. The processing container 284 takes the form of an elongated tube that is wrapped about the spool element 286 before use. The bowl and spool element 286 are pivoted on a yoke between an upright position and a suspended position. In operation, the centrifuge 272 rotates the suspended bowl and spool element 286 about an axis, creating a centrifugal field within the processing chamber 282 of container 284. Details of the mechanism for causing relative movement of the spool 286 and bowl elements as just described are disclosed in U.S. Pat. No. 5,360,542, the contents of which is also incorporated by reference herein in its entirety.

As seen in FIG. 10, the disposable processing set 274 may include the flexible processing container 284, as well as additional containers, such as a container 290 for supplying anticoagulant, a waste container 292 for collecting waste from one or more steps in a process, a container 294 for holding saline or other wash or resuspension medium, a container 296 for collecting plasma, as well as other containers 298. The set 274 also may include inlet line 300, an anticoagulant (AC) line 302 for delivering AC from container 290, an RBC line 304 for conveying red blood cells from chamber 282 of container 284 to a container 306, a platelet-poor plasma (PPP) line 308 for conveying PPP to container 296 and line 310 for conveying other fluids to and from separation chamber 282 and the containers 298. In addition, the blood processing set 274 includes one or more venipuncture needle(s) for accessing the circulatory system of the patient. As shown in FIG. 10, set 274 includes an inlet needle 312 attached to the inlet line 300 and a return needle 314 attached to a return line 316; in an alternative embodiment, a single needle can serve as both the inlet and outlet needle.

Fluid flow through set 274 is preferably driven, controlled and adjusted by the controller 260 in cooperation with the pumps 266, valves 268, and sensors 262, the details of which are described in the previously mentioned U.S. Pat. No. 5,868,696. In a general sense, blood is drawn from the patient via the inlet needle 312 into the inlet line 300, where it passes through one or more of the cassettes 276, 278, 280 and may be processed in the processing chamber 282. The containers 290, 292, 294, 296, 298, 306 are also connected via the cassettes 276, 278, 280 to the processing chamber 282, and fluids may be drawn from or passed to the containers 290, 292, 294, 296, 298, 306 as a consequence of the operation of the cassettes 276, 278, 280 and the chamber 282 (and associated pumps and spool/bowl element). Fluid is returned to the patient along return line 316 via return needle 314.

Figure 11:
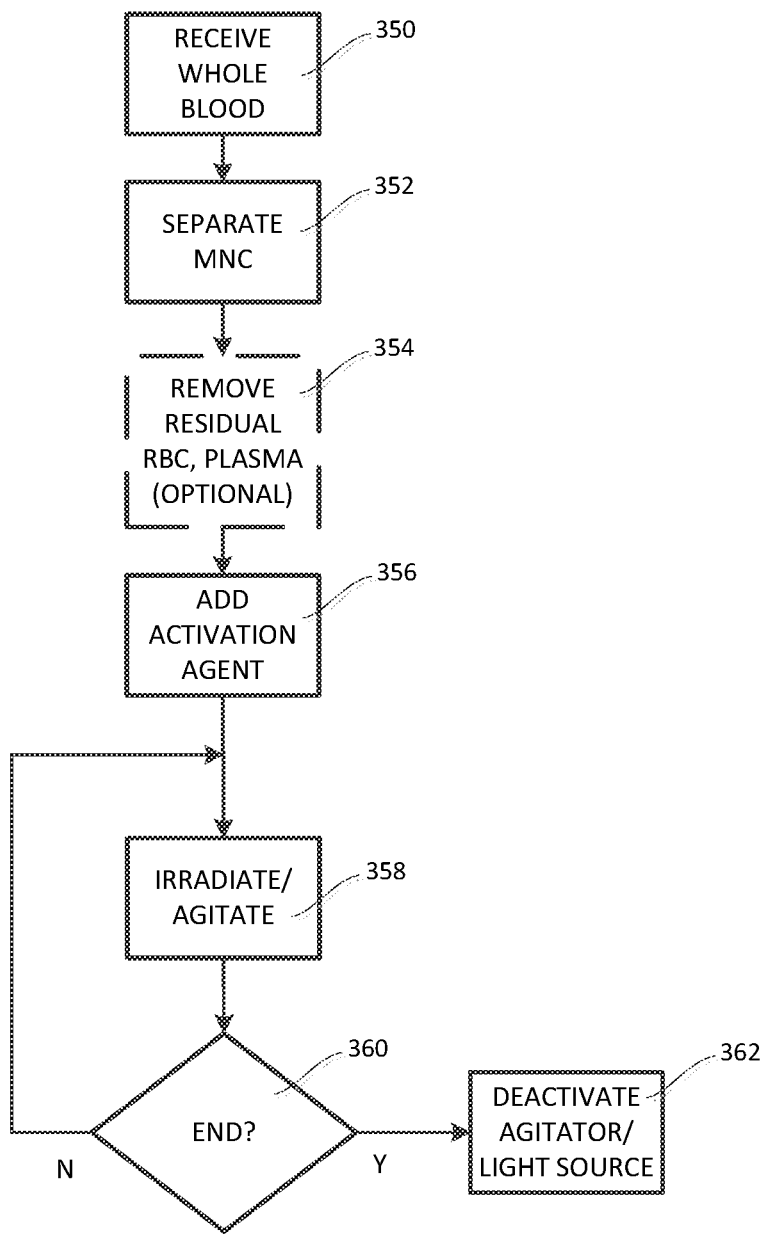
FIG. 11 is a flowchart illustrating an embodiment of a method of operating the medical system of FIG. 6.

The system 250 may be used, for example, for the treatment of mononuclear cells with ultraviolet light as illustrated in FIG. 11. First, separator 252 receives whole blood that has been withdrawn from a patient (block 350). The whole blood is introduced into separation chamber 282 of separator 252, where the whole blood is subjected to a centrifugal field. The centrifugal field separates the target cell population, i.e., mononuclear cells (MNC), from red blood cells (RBC), platelets and plasma (block 352). The red blood cells and platelets separated at this stage may be returned to the patient, or optionally may be diverted to a container (e.g., container 306) for further processing.

As a practical matter, a quantity of red blood cells and plasma typically remains in suspension with the separated mononuclear cells. These red blood cells and plasma may be optionally removed prior to further processing (block 354). The removal of the residual red blood cells and plasma can have the effect of reducing irradiation time from, for example, approximately 30 minutes to approximately 5 minutes.

According to different embodiments of the method of treating mononuclear cells with ultraviolet light described herein, different methods for removing the residual red blood cells and plasma may be used when this action is optionally included. For example, according to one embodiment, a lysing agent is added to the suspended mononuclear cells, and then the suspension is incubated to activate the lysing agent to disintegrate or dissolve the red blood cells. The suspension is then washed using separator 252 to remove plasma and hemoglobin freed by the lysis of the red blood cells. The washed, lysed suspension is then re-suspended. Alternatively, the residual red blood cells may be removed from the MNC suspension by using immunogenic cell separation techniques, in which paramagnetic beads coated with antibodies are used to bind the beads to antigens on the surface of the red blood cells, and the suspension is subjected to a magnetic force to separate the red blood cells, or additional density gradient separation (using, e.g., the centrifuge) may be performed.

In any event, the MNC suspension is subsequently combined with an activation agent, such as 8-methoxypsoralen (8-MOP), (block 356), and then exposed to ultraviolet light (block 358) with the intent to obtain a treated cell product. In one non-limiting example, during treatment, the mononuclear cell product may be exposed to UV LEDs having a wavelength in the UVA range of about 320 nm to 400 nm for a selected period of time, preferably 5 minutes or less, resulting in an average UVA exposure of approximately 0.5-5.0 J/cm2. As indicated at block 358, the container in which the MNC suspension and activation agent may also be moved to agitate the contents.

A determination is made at block 360 whether the processing has been completed. If the processing is completed, the light source 110, 112 (and agitator 210) may be deactivated at block 362, and the treated cells may be reinfused to the patient. Otherwise, the process may return to block 358, and processing may continued until the determination is made at block 360 to terminate the process.

Automated control of the MNC collection and the irradiation treatment may be affected by the microprocessor-based controller of the respective separation device 252 and irradiation device 100 with some operator input for each device. Alternatively, operation of both separation device 252 and irradiation device 100 and the process steps carried out by each may be remotely controlled by a separate controller (e.g., a computer) that communicates with both.

Other Aspects

Aspect 1. An irradiation device comprising:
a fluid treatment chamber having first and second opposing sides configured to receive a biological fluid container therebetween; and
at least one light source disposed adjacent at least one of the first and second sides of the fluid treatment chamber, the at least one light source comprising:
a light guide having a front planar surface that defines in part the at least one of the first and second sides of the fluid treatment chamber, and
at least one light emitting diode (LED) disposed at an edge of the light guide outside the fluid treatment chamber and configured to direct light into the light guide,
the light guide having a back surface opposite the front planar surface, the back surface with one or more reflectors that depend into the light guide in the direction of the front surface.

Aspect 2. The irradiation device of aspect 1, wherein the one or more reflectors are each defined by at least one hemicylindrical shape that depends into the light guide from the back surface in the direction of the front surface.

Aspect 3. The irradiation device of aspect 2, wherein the light guide has a first axis and the at least one LED is disposed along the first axis, and a second axis transverse to the first axis and the at least one hemicylindrical shape is disposed along the second axis.

Aspect 4. The irradiation device of aspect 3, wherein the light guide has opposing first and second ends disposed facing each other along the second axis, the at least one hemicylindrical shape disposed along the second axis continuously between the first end and the second end.

Aspect 5. The irradiation device of aspect 2, wherein the one or more reflectors comprises a plurality of hemicylindrical shapes that depend into the light guide from the back surface in the direction of the front surface, the plurality of hemicylindrical shapes being equally disposed along the back surface,
the light guide has a first axis and the at least one LED is disposed along the first axis, and a second axis transverse to the first axis and the plurality of hemicylindrical shapes are disposed along the second axis, and
the light guide has opposing first and second ends disposed facing each other along the second axis, each of the plurality of hemicylindrical shapes is disposed along the second axis continuously between the first end and the second end Aspect 6. The irradiation device of any one of aspects 1-5, wherein the at least one LED comprises a UV light-emitting LED.

Aspect 7. The irradiation device of any one of aspects 1-6, wherein the at least one LED comprises an array of LEDs.

Aspect 8. The irradiation device of any one of aspects 1-7, wherein the at least one light source comprises a first LED mounted at a first edge of the light guide and a second LED mounted at a second, opposite edge of the light guide, the first LED facing the second LED along the light guide and the second LED facing the first LED along the light guide.

Aspect 9. The irradiation device of any one of aspects 1-8, wherein a first light source is disposed adjacent the first side of the fluid treatment chamber, and a second light source is disposed adjacent the second side of the fluid treatment chamber.

Aspect 10. The irradiation device of aspect 9, further comprising:
a base and a lid pivotally attached to the base,
the base having a base surface and the lid having a lid surface, the base surface defining the first opposing side of the fluid treatment chamber, and the lid surface defining the second opposing side of the fluid treatment chamber.

Aspect 11. The irradiation device of any one of aspects 1-10, further comprising a tray with a translucent floor configured to be disposed between the at least one light source and the biological fluid container.

Aspect 12. The irradiation device of any one of aspects 1-11, further comprising a controller coupled to the at least one light source, the controller configured to automatically activate and to automatically deactivate the at least one light source.

Aspect 13. The irradiation device of aspect 12, wherein the controller comprises a processor and memory, and the processor is programmed to automatically activate and to automatically deactivate the at least one light source.

Aspect 14. The irradiation device of aspect 12 or 13, further comprising:
an agitator coupled to the fluid treatment chamber to move the fluid treatment chamber with an oscillatory motion,
the controller coupled to the agitator, the controller configured to automatically activate and to automatically deactivate the agitator.

Aspect 15. A system comprising: a cell separator configured to direct a biological fluid into a biological fluid container; and
an irradiation device comprising:
a fluid treatment chamber having first and second opposing sides configured to receive the biological fluid container; and
at least one light source disposed adjacent at least one of the first and second sides of the fluid treatment chamber,
the at least one light source comprising:
a light guide having a front planar surface that defines in part the at least one of the first and second sides of the fluid treatment chamber, and
at least one light emitting diode (LED) disposed at an edge of the light guide outside the fluid treatment chamber and configured to direct light into the light guide,
the light guide having a back surface opposite the front planar surface, the back surface with one or more reflectors that depend into the light guide in the direction of the front surface.

Aspect 16. The irradiation device of aspect 15, wherein the one or more reflectors comprises a plurality of hemicylindrical shapes that depend into the light guide from the back surface in the direction of the front surface, the plurality of hemicylindrical shapes being equally disposed along the back surface,
the light guide has a first axis and the at least one LED is disposed along the first axis, and a second axis transverse to the first axis and the plurality of hemicylindrical shapes are disposed along the second axis, and
the light guide has opposing first and second ends disposed facing each other along the second axis, each of the plurality of hemicylindrical shapes is disposed along the second axis continuously between the first end and the second end Aspect 17. The irradiation device of aspect 5 or 16, wherein the at least one LED comprises a UV light-emitting LED.

Aspect 18. The irradiation device of any one of aspects 15-17, wherein the at least one LED comprises an array of LEDs.

Aspect 19. The irradiation device of any one of aspects 15-18, wherein a first light source is disposed adjacent the first side of the fluid treatment chamber, and a second light source is disposed adjacent the second side of the fluid treatment chamber, and further comprising:
a base and a lid pivotally attached to the base,
the base having a base surface and the lid having a lid surface, the base surface defining the first side of the fluid treatment chamber, and the lid surface defining the second side of the fluid treatment chamber.

Aspect 20. The irradiation device of aspect 19, further comprising a controller coupled to the at least one light source, the controller configured to automatically activate and to automatically deactivate the at least one light source.

The invention claimed is:

1. An irradiation device comprising:
a fluid treatment chamber having first and second opposing sides configured to receive a biological fluid container therebetween; and
at least one light source disposed adjacent at least one of the first and second sides of the fluid treatment chamber,
the at least one light source comprising:
a light guide having a front planar surface that defines in part the at least one of the first and second sides of the fluid treatment chamber, and
at least one light emitting diode (LED) disposed at an edge of the light guide outside the fluid treatment chamber and configured to direct light into the light guide,
the light guide having a back surface opposite the front planar surface, the back surface with one or more reflectors that depend into the light guide in the direction of the front surface.

2. The irradiation device of claim 1, wherein the one or more reflectors are each defined by at least one hemicylindrical shape that depends into the light guide from the back surface in the direction of the front surface.

3. The irradiation device of claim 2, wherein the light guide has a first axis and the at least one LED is disposed along the first axis, and a second axis transverse to the first axis and the at least one hemicylindrical shape is disposed along the second axis.

4. The irradiation device of claim 3, wherein the light guide has opposing first and second ends disposed facing each other along the second axis, the at least one hemicylindrical shape disposed along the second axis continuously between the first end and the second end.

5. The irradiation device of claim 2, wherein:
the one or more reflectors comprises a plurality of hemicylindrical shapes that depend into the light guide from the back surface in the direction of the front surface, the plurality of hemicylindrical shapes being equally disposed along the back surface,
the light guide has a first axis and the at least one LED is disposed along the first axis, and a second axis transverse to the first axis and the plurality of hemicylindrical shapes are disposed along the second axis, and
the light guide has opposing first and second ends disposed facing each other along the second axis, each of the plurality of hemicylindrical shapes is disposed along the second axis continuously between the first end and the second end.

6. The irradiation device of claim 1, wherein the at least one LED comprises a UV light-emitting LED.

7. The irradiation device of claim 1, wherein the at least one LED comprises an array of LEDs.

8. The irradiation device of claim 1, wherein the at least one light source comprises a first LED mounted at a first edge of the light guide and a second LED mounted at a second, opposite edge of the light guide, the first LED facing the second LED along the light guide and the second LED facing the first LED along the light guide.

9. The irradiation device of claim 1, wherein a first light source is disposed adjacent the first side of the fluid treatment chamber, and a second light source is disposed adjacent the second side of the fluid treatment chamber.

10. The irradiation device of claim 9, further comprising:
a base and a lid pivotally attached to the base,
the base having a base surface and the lid having a lid surface, the base surface defining the first opposing side of the fluid treatment chamber, and the lid surface defining the second opposing side of the fluid treatment chamber.

11. The irradiation device of claim 1, further comprising a tray with a translucent floor configured to be disposed between the at least one light source and the biological fluid container.

12. The irradiation device of claim 1, further comprising a controller coupled to the at least one light source, the controller configured to automatically activate and to automatically deactivate the at least one light source.

13. The irradiation device of claim 12, wherein the controller comprises a processor and memory, and the processor is programmed to automatically activate and to automatically deactivate the at least one light source.

14. The irradiation device of claim 12, further comprising:
an agitator coupled to the fluid treatment chamber to move the fluid treatment chamber with an oscillatory motion,
the controller coupled to the agitator, the controller configured to automatically activate and to automatically deactivate the agitator.

15. A system comprising:
a cell separator configured to direct a biological fluid into a biological fluid container; and
an irradiation device comprising:
a fluid treatment chamber having first and second opposing sides configured to receive the biological fluid container; and
at least one light source disposed adjacent at least one of the first and second sides of the fluid treatment chamber,
the at least one light source comprising:
a light guide having a front planar surface that defines in part the at least one of the first and second sides of the fluid treatment chamber, and
at least one light emitting diode (LED) disposed at an edge of the light guide outside the fluid treatment chamber and configured to direct light into the light guide,
the light guide having a back surface opposite the front planar surface, the back surface with one or more reflectors that depend into the light guide in the direction of the front surface.

16. The irradiation device of claim 15, wherein:
the one or more reflectors comprises a plurality of hemicylindrical shapes that depend into the light guide from the back surface in the direction of the front surface, the plurality of hemicylindrical shapes being equally disposed along the back surface,
the light guide has a first axis and the at least one LED is disposed along the first axis, and a second axis transverse to the first axis and the plurality of hemicylindrical shapes are disposed along the second axis, and
the light guide has opposing first and second ends disposed facing each other along the second axis, each of the plurality of hemicylindrical shapes is disposed along the second axis continuously between the first end and the second end.

17. The irradiation device of claim 15, wherein the at least one LED comprises a UV light-emitting LED.

18. The irradiation device of claim 15, wherein the at least one LED comprises an array of LEDs.

19. The irradiation device of claim 15, wherein a first light source is disposed adjacent the first side of the fluid treatment chamber, and a second light source is disposed adjacent the second side of the fluid treatment chamber, and further comprising:
a base and a lid pivotally attached to the base,
the base having a base surface and the lid having a lid surface, the base surface defining the first side of the fluid treatment chamber, and the lid surface defining the second side of the fluid treatment chamber.

20. The irradiation device of claim 19, further comprising a controller coupled to the at least one light source, the controller configured to automatically activate and to automatically deactivate the at least one light source.

* * * * *